United States Patent
Easterling

(10) Patent No.: US 6,627,209 B2
(45) Date of Patent: Sep. 30, 2003

(54) SURGICAL STENT AND METHOD FOR PREVENTING OCCLUSION OF STENTED VESSELS AND CONDUITS AFTER IMPLANTATION OF STENTS

(75) Inventor: W. Jerry Easterling, 8400 Blanco Rd., San Antonio, TX (US) 78216

(73) Assignee: W. Jerry Easterling, San Antonio, TX (US)

( * ) Notice: Subject to any disclaimer, the term of this patent is extended or adjusted under 35 U.S.C. 154(b) by 0 days.

(21) Appl. No.: 09/839,572

(22) Filed: Apr. 20, 2001

(65) Prior Publication Data

US 2002/0004678 A1 Jan. 10, 2002

Related U.S. Application Data

(63) Continuation-in-part of application No. 09/514,796, filed on Feb. 28, 2000, now abandoned, which is a continuation-in-part of application No. 09/128,103, filed on Aug. 3, 1998, now Pat. No. 6,031,005.

(51) Int. Cl.$^7$ .............................. A61F 2/02; A61F 2/06; A61K 47/30

(52) U.S. Cl. ................... 424/423; 514/772.3; 623/1.42; 623/1.43; 623/1.44; 623/1.45; 623/1.46

(58) Field of Search ................................ 424/422, 423; 514/772.3; 623/1.42, 1.43, 1.44, 1.45, 1.46

(56) References Cited

U.S. PATENT DOCUMENTS 6,143,037 A * 11/2000 Goldstein et al. ............. 623/66

\* cited by examiner

*Primary Examiner*—Carlos Azpuru
(74) *Attorney, Agent, or Firm*—David G. Henry

(57) ABSTRACT

The invention is of the design for, and a method of use of, an improved surgical stent. The stent is coated with a slow-release calcium channel blocker agent which interrupts the accumulation or deposition of fibrotic tissue as occurs in the process of re-occlusion of the vessel, orifice, or conduit as attends the use of conventional stents.

1 Claim, No Drawings

SURGICAL STENT AND METHOD FOR PREVENTING OCCLUSION OF STENTED VESSELS AND CONDUITS AFTER IMPLANTATION OF STENTS

This is a continuation-in-part with respect to U.S. application, Ser. No. 09/514,796 filed Feb. 28, 2000, now abandoned, which was a continuation-in-part of U.S. application Ser. No. 09/128,103, filed Aug. 3, 1998 now U.S. Pat. No. 6,031,005, from which application and its parent application priority is here claimed under 35 U.S.C. §120.

BACKGROUND OF THE INVENTION

1. Field of the Invention

The present invention relates to the surgical implantation of stents, such as, for example, in the treatment of arterial occlusion in heart disease, and ureteral occlusion in kidney disease or injury.

2. Background Information

In surgical or other related invasive medicinal procedures, the insertion and expansion of stent devices in blood vessels, urinary tracts or other difficult to access places for the purpose of preventing restenosis, providing vessel or lumen wall support or reinforcement and for other therapeutic or restorative functions has become a common form of long-term treatment. Typically, such prosthesis are applied to a location of interest utilizing a vascular catheter, or similar transluminal device, to carry the stent to the location of interest where it is thereafter released to expand or be expanded in situ. These devices are generally designed as permanent implants which may become incorporated in the vascular or other tissue which they contact at implantation.

Implanted stents have also been used to carry medicinal agents, such as thrombolytic agents. U.S. Pat. No. 5,163,952 to Froix discloses a thermal memoried expanding plastic stent device which can be formulated to carry a medicinal agent by utilizing the material of the stent itself as an inert polymeric drug carrier. Pinchuk, in U.S. Pat. No. 5,092,877, discloses a stent of a polymeric material which may be employed with a coating associated with the delivery of drugs. Other patents which are directed to devices of the class utilizing bio-degradable or bio-sorbable polymers include Tang et al, U.S. Pat. No. 4,916,193, and MacGregor, U.S. Pat. No. 4,994,071. Sahatjian in U.S. Pat. No. 5,304,121, discloses a coating applied to a stent consisting of a hydrogel polymer and a preselected drug; possible drugs include cell growth inhibitors and heparin. A further method of making a coated intravascular stent carrying a therapeutic material in which a polymer coating is dissolved in a solvent and the therapeutic material dispersed in the solvent and the solvent thereafter evaporated is described in Berg et al, U.S. Pat. No. 5,464,650, issued Nov. 5, 1995 and corresponding to European patent application 0 623 354 A1 published Nov. 9, 1994.

Health statistics show that nearly 1.5 million people in the U.S. have abdominal aneurysms, and 190,000 cases are diagnosed annually. More than 700,000 U.S. patients with coronary artery disease have stents employed in order to relieve blockages that cause chest pain and oftentimes lead to heart attack. As many as 30,000 Americans are diagnosed each year with bile duct blockage.

The design and manufacture of stents is well known. Additional examples of stents and their designs are shown in U.S. Pat. Nos. 6,187,037, 6,187,015, 6,183,508, 6,179,867, 6,168,620, 6,159,239, 6,159,227, 5,421,955, and 5,135,536, just to name a few, recent references. Also well known is the design and manufacture of stents which are coated in some way for therapuetic benefit. U.S. Pat. Nos. 6,153,252, 6,136,006, 6,096,070, 5,922,393, 5,897,911, 5,980,551, and 5,837,313 all teach some form of coating stents to achieve some therapeutic advantage over non-coated stents.

Although stents provide a less invasive method of treatment or repair as opposed to surgery, they do possess one major disadvantage. As the area around the stent heals, the scar tissue that accumulates often invades the area held open by the stent and causes the area to occlude with scar tissue. This process is called reactive fibrosis. Oftentimes, in these cases, smaller stents are placed inside the original larger stents in order to open up a stent occluded with scar tissue.

Current research includes the coating of stents with drugs to reduce excessive scarring. Early studies have reported the coating of stents with rapamycin, an immune system suppressant.

A most recent development in the attempt to curb restenosis is taught in U.S. Pat. No. 6,159,142. However, an even more recent Associated Press article (appearing on Mar. 19, 2001 in the San Antonio Express News) indicates that radiation (the means for preventing restenosis taught in the '142 patent) is not proving effective in keeping arteries open. The article describes the tendency of angioplasties to "go bad" as one of the most vexing and persistent problems in all of cardiology.

In view of the above, it would be highly beneficial and, in some cases, a life-saving event, to provide the design for an improved surgical stent which actively resists the processes which otherwise would lead to re-occusion of the opened vessel or conduit.

SUMMARY OF THE INVENTION

It is an object of the present invention to provide an improved surgical stent.

It is another object of the present invention to provide an improved treatment methodology involving the use of a surgical stent, which stent is modified in such a way that processes leading to re-occlusion of the vessel or conduit, in absence of such modifications, are prevented or, at least, minimized.

In satisfaction fees and related objects, the present invention provides the design for, and a method of use of, an improved surgical stent. The stent of the present invention is coated with a slow-release calcium channel blocker which, in turn, interrupts the accumulation or deposition of fibrotic tissue as occurs in the process of re-occlusion as attends the use of conventional stents.

DETAILED DESCRIPTION OF THE PREFERRED EMBODIMENT

It is proposed that the superstructure of stents (the wire mesh, coiled wire, or any other form in which a stent may be found) be coated with a biodegradable carrier material such as poly(epsilon-caprolactone) that has been impregnated with a sustained release calcium channel blocker (preferably verapamil). Verapamil can be rendered a sustained release property by treatment with other chemicals such as stearic acid. Processes for coating a stent in such a manner to provide slow-release of therapeutic agents is specifically shown in U.S. Pat. No. 6,210,436 issued to Weadlock, the relevant disclosure of which is incorporated herein by reference.

A stent coated with sustained release verapamil will inhibit the excess accumulation of scar tissue for two to three months during the healing process, thereby eliminating the need for radiation treatment of excess scarring or the additional placement of a smaller stent within a larger stent that has been occluded with scar tissue.

Because verapamil is an already approved, widely used systemic medication with the capacity for ameliorating hypertension, without creating any significant risk of hypotension, the safety of the use of verapamil in the instant context will be of no serious concern.

Because of the mechanism of action of verapamil in combating aberrant fibrotic tissue manifestations or accumulations, and of the fact that other calcium channel blockers are also known to have the same effect when administered in the same manner as a known efficatious administration of verapamil, it should be understood that verapamil is merely the preferred calcium channel blocker to be used in practicing the present invention. Alternative calcium channel blocker agents which may be substituted for verapamil (subject to confirming safety in this context) include benzothiazepines (Diltiazem, for example), dihydropyridines (Amlodipine, Felodipine, Isradipine, Nicardipine, Nifedipine, Nimodipine, or Nisoldipine), and the fast sodium inward channel inhibitor—Bepridil.

As mentioned before, the technology for manufacturing stents, and for coating them with beneficial compounds is well known. The disclosures of the above-cited patents in this regard are incorporated herein by reference, to the extent necessary to provide an enabling disclosure.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method for providing a re-occlusion resistant stent implantation to a human patient comprising the steps of:
    selecting a coated stent for implantation in human vessels for creating and sustaining openings therein and for preventing re-occlusion thereof after implantation, said coated stent comprising:
        a stent superstructure;
        a biodegradable carrier material applied to said stent superstructure to form a coating thereof,
        a calcium channel blocker agent carried by said biodegradable carrier material; and
    implanting said coated stent into a human vessel, orifice or conduit.

* * * * *